(12) United States Patent  (10) Patent No.: US 8,502,968 B2
Yavets-Chen et al.  (45) Date of Patent: Aug. 6, 2013

(54) SURFACE SCANNING DEVICE (75) Inventors: Yehuda Yavets-Chen, Caesaria (IL); Dekel Tzidon, Hod Hasharon (IL)

(73) Assignee: Ceramicam Ltd., Rosh Haain (IL)

( * ) Notice: Subject to any disclaimer, the term of this patent is extended or adjusted under 35 U.S.C. 154(b) by 135 days.

(21) Appl. No.: 13/063,295

(22) PCT Filed: Sep. 10, 2009

(86) PCT No.: PCT/IL2009/000886
§ 371 (c)(1),
(2), (4) Date: Apr. 11, 2011

(87) PCT Pub. No.: WO2010/029549
PCT Pub. Date: Mar. 18, 2010

(65) Prior Publication Data
US 2011/0181873 A1  Jul. 28, 2011

Related U.S. Application Data (60) Provisional application No. 61/136,537, filed on Sep. 12, 2008.

(51) Int. Cl.
*G01N 21/00* (2006.01)
(52) U.S. Cl.
USPC ............................................. 356/237.2
(58) Field of Classification Search
USPC ............................................. 356/237.2
See application file for complete search history.

(56) References Cited

U.S. PATENT DOCUMENTS

| | | | |
|---|---|---|---|
| 3,667,846 A | 6/1972 | Nater et al. | |
| 4,975,972 A | 12/1990 | Bose et al. | |
| 5,168,322 A | 12/1992 | Clarke et al. | |
| 5,185,638 A | 2/1993 | Conzola et al. | |
| 5,436,722 A | 7/1995 | Baldwin | |
| 5,864,394 A | 1/1999 | Jordan et al. | |
| 5,897,195 A | 4/1999 | Choate | |
| 7,072,034 B2 * | 7/2006 | Rosengaus et al. | 356/237.5 |
| 7,357,529 B2 | 4/2008 | Choate et al. | |
| 7,453,563 B2 * | 11/2008 | Rudert et al. | 356/239.1 |
| 7,671,992 B2 * | 3/2010 | Ehbets et al. | 356/416 |
| 2007/0052953 A1 | 3/2007 | Hill | |

FOREIGN PATENT DOCUMENTS

WO  WO 2008/016590 A2  2/2008

OTHER PUBLICATIONS

International Search Report for PCT Application No. PCT/IL2009/000886 mailed on Jan. 27, 2010.
Supplementary European Search Report for European Application No. 09812780.6 mailed Jan. 24, 2012.

* cited by examiner

*Primary Examiner* — Tu Nguyen
(74) *Attorney, Agent, or Firm* — Pearl Cohen Zedek Latzer, LLP (57) ABSTRACT A surface scanning device for inspecting a product surface includes an illumination module and an image acquisition device. The illumination module is designed to illuminate the product surface with illumination of substantially uniform illuminance. The illumination module is also designed to configure a configurable range of angles of incidence of the illumination on the product surface. The image acquisition device images the illuminated area.

14 Claims, 5 Drawing Sheets

SURFACE SCANNING DEVICE

CROSS-REFERENCE TO RELATED APPLICATIONS

This application is a National Phase Application of PCT International Application Number PCT/IL2009/000886, International Filing Date Sep. 10, 2009, entitled "Surface Scanning Device", published on Mar. 18, 2010 as International Publication Number WO 2010/029549, which claims priority of U.S. Provisional Patent Application No. 61/136,537, entitled "Surface Defects Inspection System", filed on Sep. 12, 2008, both of which are incorporated herein by reference in their entirety.

FIELD OF THE INVENTION

The present invention relates to quality control. More particularly, the present invention relates to a device for scanning a product surface.

BACKGROUND OF THE INVENTION

Quality inspection is an important component of a production line. Defects in products that are not detected in the production plant, and that find their way to a customer, may cause significant problems or inconvenience to the customer, as well as damage to the reputation of the manufacturer.

For example, a production line may be configured to produce ceramic tiles. Defects in a tile may include cracks or scratches, or areas that have been colored with the wrong hue. Defects may be caused by failure of one or more components of the production line. Failure to detect a defect in the production line soon after the appearance of the failure may result in the production of a large quantity of defective tiles. Detection of the defects at a later stage, such as during a final inspection or during inspection by a customer receiving a shipment of tiles may result in rejection of a large quantity of tiles. Therefore, it is desirable to include an inspection step in a production line.

An inspection apparatus employed in an inspection step of a production should be such as to enhance the ability of an operator to detect defects with a large degree of reliability and consistency. For example, the apparatus may be configured to enhance the ability to distinguish a surface defect against a background of intentional or acceptable surface features. Such an inspection apparatus on a production line may result in immediate detection of defects as they are formed, possibly enabling immediate adjustment of production parameters so as to prevent formation of further defects. For example, illumination of the surface may be such as to emphasize surface defects. In some cases, an inspection apparatus may include an imaging system and image processing in order to identify defects. For example, Bose et al. in U.S. Pat. No. 4,975,972 describe surface inspection in which image processing is used to adjust gray scale levels so as to isolate an image of a defect from the remainder of an acquired image. Other systems, such as those described by Clarke et al. (U.S. Pat. No. 5,168,322) and Jordan, III et al. (U.S. Pat. No. 5,864,394) utilize comparisons between acquired images, typically in nominally flat surfaces. Nater et al. in U.S. Pat. No. 3,667,846 describes an apparatus for measuring microscopic height differences in a surface.

An apparatus for enhancing the ability to inspect products in a production line may be particularly useful for detection of surface geometrical defects in products containing possibly textured flat facets. However, implementing such enhanced inspection may be difficult. For example, a single production line may produce a family of similar products, but with significant differences among the individual products. In such a case, it may be difficult to configure a general purpose apparatus for enhancing inspection of all products produced by the production line. For example, a production plant for producing ceramic tiles may be used to produce a wide variety of tile designs containing a variety of surface finishes. For example, at one extreme a polished, glossy, or shiny surface that reflects light specularly, and at the other extreme, a matte surface may reflect light diffusively.

In addition, a product surface may be intentionally designed with texture or with raised geometrical patterns or other designs in relief. A detection system must be configured to enable distinguishing such intentional surface features from surface defects. For example, a production line for the production of ceramic tiles may be used to produce various tile designs where the intentional patterning may vary from design to design. In addition, a single tile design may include acceptable variations in patterning that may vary from tile to tile.

Existing inspection systems are often not configurable for a wide variety of product surfaces. As a result, such systems may not detect defects in the surface of a given product design with sufficient reliability. Such systems may yield false positive (detection of a defect where none exists) or false negative (failure to detect an existing defect) results. False positive results may result in unnecessarily delays in production, or in ignoring the results yielded by the inspection system. False negative results may result in production of an unacceptably large number of defective products.

On the other hand, reconfiguring an inspection system for inspection of a different product design may typically involve extensive retooling or reprogramming of the system. Thus, the scope of application of such a system may be limited to specific defects on a specific type of surface.

Thus, there is a need for an inspection system that enhances the ability to distinguish between intentional surface features and surface defects, and which may be readily and reproducibly reconfigured for inspecting a wide variety of surface types.

It is an object of the present invention to provide a surface scanning system that is configurable to detect defects of different characteristics in a variety of surface types.

Other aims and advantages of the present invention will become apparent after reading the present invention and reviewing the accompanying drawings.

SUMMARY OF THE INVENTION

There is thus provided, in accordance with some embodiments of the present invention, a surface scanning device for inspecting a product surface including an illumination module for illuminating the product surface with illumination of substantially uniform illuminance, and for configuring a configurable range of angles of incidence of the illumination on the product surface; and including an image acquisition device for imaging the illuminated area.

Furthermore, in accordance with some embodiments of the present invention, the illumination module includes an illumination source.

Furthermore, in accordance with some embodiments of the present invention, the configurable range of angles of incidence is selectable from two or more ranges of angles of incidence Furthermore, in accordance with some embodiments of the present invention, the configurable range of angles of incidence is adjustable.

Furthermore, in accordance with some embodiments of the present invention, the illumination module includes a diffuser.

Furthermore, in accordance with some embodiments of the present invention, the diffusing power of the diffuser is adjustable.

Furthermore, in accordance with some embodiments of the present invention, the illumination module includes an aperture.

Furthermore, in accordance with some embodiments of the present invention, the aperture is adjustable.

Furthermore, in accordance with some embodiments of the present invention, the illumination module includes a converging lens.

Furthermore, in accordance with some embodiments of the present invention, the lens comprises one or more Fresnel lenses.

Furthermore, in accordance with some embodiments of the present invention, at least one of the Fresnel lenses is curved.

Furthermore, in accordance with some embodiments of the present invention, the Fresnel lenses comprise two adjacent Fresnel lenses, wherein flat surfaces of the two Fresnel lenses face each other.

Furthermore, in accordance with some embodiments of the present invention, the image acquisition device comprises a line camera.

Furthermore, in accordance with some embodiments of the present invention, the illumination module and the image acquisition device are arranged at such that an axis of a beam of illumination produced by the illumination module and a line of sight of the image acquisition device form substantially equal and opposite angles with a normal to the product surface.

Furthermore, in accordance with some embodiments of the present invention, a location and orientation of the illumination module, the image acquisition device, or both is adjustable.

Furthermore, in accordance with some embodiments of the present invention, the illumination module produces illumination in at least two different spectral ranges, each spectral range having separately configurable range of angles of incidence, and the image acquisition device includes sensors each responsive to one of the different spectral ranges.

Furthermore, in accordance with some embodiments of the present invention, the illumination module comprises a stack of spectral filters, each spectral filter of the stack configured to block transmission of at least one of the different spectral ranges while transmitting at least one of the different spectral ranges, each spectral filter including an aperture for transmitting all of the different spectral ranges.

Furthermore, in accordance with some embodiments of the present invention, the aperture of a spectral filter of the stack of spectral filters is adjustable.

Furthermore, in accordance with some embodiments of the present invention, the illumination module comprises an array of sources of illumination, each source of illumination configured to produce illumination in one of the different spectral ranges, the sources being controllable such the sources in a region of the array producing illumination in one of the different spectral ranges may be turned on independent of sources in other regions of the array, and independent of sources producing illumination in a different spectral range.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF EMBODIMENTS

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

A surface scanning system, in accordance with embodiments of the present invention, includes an adjustable illumination system for illuminating a surface of a product with adjustable illumination. Typically, the adjustment includes adjusting the range of angles of incidence of the illumination on the surface. The surface scanning system also includes one or more cameras or other image acquisition devices for acquiring illuminating radiation that is reflected from the illuminated surface and forming an image. The image may be inspected visually. Alternatively, the image may be processed by a processor for detection of surface defects in the scanned surface. The system may include a control system for controlling components of the inspection system. For example, components of the illumination system may be adjusted via a control system.

A scanned surface may include one or more undesirable defects. The surface scanning system may be expected to enable detection of such defects. The surface may include, in addition, intentional two or three dimensional design features, such as patterns, designs, or texture. The surface scanning system may be expected to enable distinguishing undesirable surface defects from such acceptable or desirable intentional surface features. The illumination may be adjusted to attain an optimum illumination. Illumination may be considered optimized when visibility or detectability of defects in an acquired image is enhanced relative to a background pattern that may include intentional features.

An illumination system of an inspection system in accordance with embodiments of the present invention may be provided with one or more adjustable components. The adjustable components may be adjustable so as to achieve a desired illumination of a product surface. For example, adjustable components may include a variable diffuser, a variable aperture, an adjustable lens, and an adjustable mount for rotating the components as a group about a product surface. The illuminating light may be emitted by a light source. For the purpose of this description, light is considered to include electromagnetic radiation of the visible, ultraviolet, and infrared spectral ranges, or any other radiation that may be reflected off a surface and imaged. The light produced by a light source may traverse one or more adjustable components of the illumination system prior to impinging on the product surface. Adjusting the adjustable components may adjust the distribution of the illuminating radiation and the angles of incidence of the illuminating radiation on the product surface. The adjustable components may be adjusted until a best possible illumination is achieved.

For example, a scanning device in accordance with embodiments of the present invention may be incorporated into an inspection device for inspecting a production line for producing ceramic tiles. A typical ceramic tile is in the form of a thin rectangular plate, with two sides and four narrow edges. A surface on one side of the tile is typically finished, for example by glazing or painting. At the edges of the tile, the edges of the finished surface typically curve to form a convex meniscus, which is also finished. The side of the tile opposite the finished surface, the biscuit, as well as an adjacent part of the edge, typically remains unfinished. Typically, the tile is designed for installation in a wall, floor, countertop, or other part of a structure or building. When installed, typically only the finished surface and meniscus are visible.

The finished surface may be provided with raised or recessed surface features arranged to form a decorative or functional pattern or design. Typically, the finished surface, and, optionally, the meniscus and edge of the tile, may be inspected for defects. The unfinished surface typically remains in a rough state and does not require inspection for small defects. A typical defect in the finished surface or meniscus may include an inclusion, crack, chip, scratch, or other sharp edged deviation from a smooth surface. Edges of such defects typically include steeply sloped walls. The slopes of walls at an edge of a typical intentionally introduced surface feature are generally smaller, sloping more gradually than the walls at an edge of a defect.

Since the variations in surface height at the edge of a defect are typically steeper than the variations at the edge of an intentional feature, appropriately configured illumination may enhance the visibility of a defect relative to a feature. For example, the illumination may be configured such that a wall of a defect creates a shadow while the wall of an intentional feature does not. If an illuminated surface is at least partially specularly reflecting the illumination may be configured such that a wall of a defect reflects illuminating light away from an image acquisition device such as a camera, while a wall of an intentional feature does not.

An illumination system for a surface scanning system, in accordance with some embodiments of the present invention, typically includes a light source. In a typical application of the inspection system, a surface of a product is transported in a longitudinal direction of motion past the illumination system and the radiation detection system of the surface scanning system. A typical surface scanning system may then be configured to illuminate and acquire reflected radiation from a narrow elongated transverse area of the product surface. The long axis of the elongated transverse area is at an oblique angle to, typically perpendicular to, the longitudinal direction of motion. For example, the radiation source may include one or more fluorescent lamp tubes, or other elongated electric light bulbs or radiation sources. Typically, the lamp tubes are oriented parallel to one another with their cylindrical axes oriented perpendicular to the direction of transport. Typically, the lamp tubes may be arranged in a recessed cavity with diffusively reflecting walls. For example, the walls of the cavity may be coated with a highly reflective diffuse white paint. Such a diffusively reflecting cavity may tend to reduce spatial variations in the spatial distribution of the intensity of light emitted by the source. Alternatively to including a light source, illumination system may direct illumination produced by an external illumination source toward a surface to be scanned.

An illumination system of a surface scanning system in accordance with embodiments of the present invention may include adjustable elements for adjusting or optimizing characteristics of the beam. Such adjustments may affect brightness of the beam, uniformity of the beam, an average angle of incidence of the beam on a product surface, a range of incident angles at a point of the product surface, and the shape or form of the beam incident on the product surface. For example, the intensity of the output of a radiation source may be adjustable. Also, the position and orientation of the illumination system may be adjustable so as to adjust an angle of incidence and to adjust the uniformity of the illumination. For example, the illumination system may be mounted in a movable fashion on one or more tracks. As another example, the beam may be collimated or may be configured to focus or converge on the product surface. Adjustment of adjustable components of the illumination system then may modify collimation or the convergence.

An image acquisition device of a surface scanning system in accordance with embodiments of the present invention may be configured to image light reflected from an illuminated area of the product surface. For example, the image acquisition device may include a line scan camera, which is designed to acquire an image from a narrow field of view focused onto a narrow array or row of pixels. For example, a line scan camera may include a detector array in the form of a single row of charge-coupled device (CCD) detectors. The linear field of view may typically be oriented parallel to the transverse direction, perpendicular to a direction of motion of a surface being scanned. In this manner, the entire product surface may be scanned as the product is moved past the camera. The orientation and other operating parameters of the image acquisition device may be determined partly on the basis of the configuration of the illumination system and on the properties of the surface being inspected. For example, the image acquisition device may include a camera designed to capture the entire sample surface or portion of it.

An illumination system in accordance with embodiments of the present invention may include a diffuser. The purpose of the diffuser is to reduce spatial intensity variations in the illumination emitted by the light source and to enable uniform illuminance on a scanned region of the product surface. For example, an array of lamp tubes may include gaps between the tubes. A diffuser may diffuse the emitted light such that variations in illumination caused by the gaps are reduced or substantially eliminated. A diffuser may be configured with spatial regions of different diffusive power. For example, a diffuser may be configured with varying diffusive power along a linear axis in order to compensate for differences in angle of incidence along that axis. A diffuser may include a stack of diffusers with appropriate gaps between the separate diffusers.

The diffuser may be adjustable with adjustable diffusive power. Adjustment of the diffusive power may affect the uniformity of the illumination. For example, a variable diffuser may include a liquid crystal window whose diffusive power is controllable via an applied voltage. Diffusive power of a liquid crystal variable diffuser may then be adjusted by adjusting the applied voltage. Alternatively, a variable diffuser may include a rectangular or circular tray holding an array of diffusers of different diffusive power. The tray may then be translated or rotated so as to align one of the diffusers with the emitted beam. Alternatively, a diffusive film with regions of various diffusive powers may be scrolled to expose a desired region. Movement of the tray may be effected either by mechanical or electric adjustment controlled directly by an operator, or via a controller component of the system. A diffuser may include regions of spatially varying diffusive power that are configured to cooperate with known non-uniformities of the light source in order to produce a substantially uniform illumination.

An illumination system of a surface scanner in accordance with embodiments of the present invention typically includes an adjustable iris with a variable aperture for limiting the angular extent of a beam. Typically, the iris is in the form of two plates that partially overlap at their distal ends. The distal ends of the two plates include identical triangular notches. Overlapping the distal ends in a symmetric manner causes the overlapping notches to produce a diamond shaped aperture. Moving the plates toward or away from one another in a symmetric manner adjusts the size of the aperture. Typically, movement of the plates is effected by means of one or more electric motors controlled by a controller. Alternatively, the aperture size, rather than being continuously variable, may be selectable from a selection of discrete sizes. For example, one or more fixed apertures may be provided, of which one is selectable.

An illumination system typically includes a focusing element, such as a converging lens, to direct a beam of light that traverses the aperture onto a surface to be scanned. The lens may be configured such as to increase the uniformity of the illumination. For example, the lens may be designed intentionally with aberrations that tend to produce a somewhat defocused beam. Typically, the lenses used are large compared with the size of the illuminated area. Typically, a section of a plano-convex Fresnel lens may be used. For example, a rectangular section cut from the Fresnel lens may be used. Typically, two similar Fresnel lenses may be mounted so as to produce a compound lens with a shorter (approximately half) focal length than either Fresnel lens alone. As is known in the art, positioning the lenses so that their grooved surfaces face each other reduces aberrations, while positioning the lenses such that their planar surfaces face one another increases the aberrations. Thus, a typical illumination system of a surface scanner may include a pair of Fresnel lenses arranged with their planar surfaces facing one another. This may increase the aberrations, thus creating a more uniform illumination. Aberrations may be further increased by mechanically bending at least one of the plano-convex Fresnel lenses into a curved shape. A curved shape may result in a lens that is an approximate equivalent to a concave-convex (meniscus) lens shape. Alternatively to a Fresnel lens, an appropriately shaped lens, mirror, prism, or any other element capable of directing a beam may be provided. One or more components of a focusing element may be moveable so as to vary the location of a focus, or a focal length, of the focusing element.

Typically, a lens is arranged such that an appropriate component of the illumination system, typically an aperture, is located near one focus of the lens. In this manner, the lens produces a collimated beam of light focused at infinity. The collimated beam may impinge on a surface with a range of angles of incidence, described by an angle of incidence and an angular divergence. The angular divergence of the collimated beam may be determined in part by the size of the variable aperture. By adjusting the size of the variable aperture, the angular divergence of the collimated beam may be determined in a continuous or in a discrete manner.

An illumination system of a surface scanner, in accordance with embodiments of the present invention, may be adaptable to different surface characteristics and designs. The adaptation may be done by controlling one or more factors such as the illumination angle, the light source aperture size, operation of individual components of a light source, and the diffusive power of a diffuser. Typically, the aperture size alone may be adjusted.

For example, adjustment of the illumination system for a specific surface design may be performed as follows. The surface may be scanned by the surface scanning device with various configurations of the illumination system. For example, an aperture size may be adjusted. The results may be reviewed so as to identify an optimal configuration in which the optical signature of a defect is best differentiated from the optical signature of an intentional surface feature. For example, the size of the aperture may be initially increased to produce a beam with a large angular divergence. A sample surface, preferably one that is apparently free of defects, is scanned. An image acquired with a wide beam is typically uniform, with no visible variation. The size of the aperture may then be decreased and the scan repeated. This process is then repeated until the acquired image shows a non-uniform image. Typically, such a non-uniform structure may be produced by reflections from intentionally introduced surface features. Increasing the size of the aperture to that when the last uniform image was acquire is expected to produce an optimal configuration with increased contrast between surface defects and intentional features in the image. Parameters that defined the optimal configuration may then be recorded in a memory device associated with a controller, or elsewhere. Thus, whenever a product surface of similar design or characteristics is scanned, the configuration of the illumination system may be adjusted to that of the recorded configuration. The optimization procedure may be performed manually by an operator. Alternatively, the optimization procedure may be run automatically by a controller and processor running computer-controlled controls in an automated closed loop system.

Reference is now made to the accompanying figures.

Figure 1:
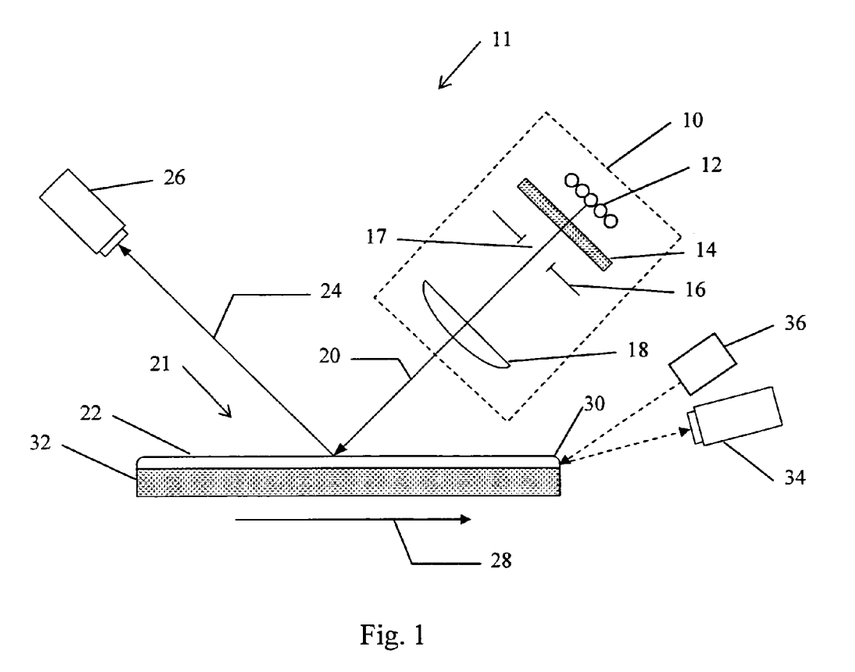
FIG. 1 is a schematic illustration of a surface scanning apparatus in accordance with embodiments of the present invention.

FIG. 1 is a schematic illustration of a surface scanning apparatus in accordance with embodiments of the present invention. Surface scanning apparatus 11 is designed to scan one or more surfaces of a product, for example, ceramic tile 21. For example, surface scanning apparatus 11 may be configured to scan finished surface 22 of ceramic tile 21, and possibly meniscus 30 of ceramic tile 21. Typically, an unfinished biscuit 32 of ceramic tile 21 may not be scanned. During scanning of a surface such as finished surface 22, the product, such as ceramic tile 21, may be conveyed by a suitable conveyance device past surface scanning apparatus 11, for example, in the direction indicated by arrow 28. Conveyance in the direction of arrow 28 may enable various areas of the surface of ceramic tile 21 to be scanned sequentially.

Surface scanning apparatus 11 includes an illumination system 10 for producing illumination represented by illuminating beam 20. Surface scanning apparatus 11 also includes one or more image acquisition devices for detecting illuminating light reflected from a product surface. For example, image acquisition devices may include camera 26 configured to detect illuminating light reflected from finished surface 22 and represented by reflected ray 24. Surface scanning apparatus 11 may optionally include one or more additional image acquisition devices to detect light that is reflected from other surfaces of ceramic tile 21. For example, one or more additional cameras, such meniscus camera 34, may be configured to detect light that is reflected from tile meniscus 30. Tile meniscus 30 may reflect illumination that was generated by illumination system 10, and possibly diverted toward tile meniscus 30. Optionally, a separate meniscus illumination system 36 may be provided for illuminating tile meniscus 30. Camera 26, camera 34, or both, may be line scan or area scan cameras.

Illumination system 10 includes light source 12. Light source 12 is designed to emit light of an appropriate spectral range, and with an appropriate spatial distribution, so as to illuminate a desired region of a product surface. For example, light source 12 may be configured to illuminate an area of finished surface 22 with visible light. In this case, light source 12 may be in the form of an array of parallel fluorescent lamp tubes.

Radiation emitted by light source 12 may traverse diffuser 14. Diffuser 14 may be controllable, with the diffusive power of diffuser 14 being controlled by one or more controls. Controlling the diffusive power of diffuser 14 may, in combination with other elements of illumination system 10, control the spatial uniformity of the intensity distribution of illuminating beam 20. In addition, depending on the geometry and relative placement of components of illumination system 10, varying the diffusive power of diffuser 14 may, in combination with other elements of illumination system 10, determine a maximum angle of incidence of radiation on finished surface 22.

Radiation that emerges from diffuser 14 may impinge on variable aperture iris 16. Variable aperture iris 16 may be adjusted to vary the dimensions of variable aperture 17 of variable aperture iris 16. For example, variable aperture 17 may be in the form of a rectangular slit of variable width, height, or both, or in the form of a circle of variable radius. Typically, variable aperture iris 16 may include two overlapping opaque panels, each with a triangular notch at its overlapping distal end. The two overlapping triangular notches form an aperture in the shape of a rhombus, or diamond. The overlapping panels are designed to slide toward and away from each other in a symmetric manner so as to adjust the size of the rhombus shaped aperture. Adjusting the dimensions of variable aperture 17 may, in combination with other elements of illumination system 10, determine the spatial distribution of illuminating beam 20. For example, the dimensions of variable aperture 17 may partially determine the size of the area of finished surface 22 illuminated by illuminating beam 20. The dimensions of variable aperture 17 may also partially determine a maximum divergence angle of illuminating beam 20 when incident on finished surface 22.

Radiation that emerges from variable aperture 17 may pass through a converging element, such as lens 18. Lens 18 may have a fixed focal length, or may include two or more elements whose relative positions are adjustable so as to vary the focal length of lens 18. Lens 18 may be movable so as to vary a position of a focal point relative to finished surface 22. Lens 18 may be designed so as to cooperate with other elements of illumination system 10 in order to provide suitable illumination of finished surface 22. For example, lens 18 may typically be configured such that variable aperture 17 is approximately a one focus of lens 18. Thus, lens 18 may form a collimated beam that may illuminate finished surface 22. For example, the focal length of lens 18 may be selected or adjusted so as to cooperate with variable aperture 17 and with diffuser 14 so as to determine a divergence angle of illuminating beam 20. As another example, lens 18 may be designed to introduce aberrations into the collimation of illuminating beam 20. Aberrations of the focused beam may tend to reduce variations in, and increase the uniformity of, the illuminance of beam 20 on finished surface 22.

Typically, lens 18 includes two rectangular sections of Fresnel lenses. Typically, the two sections are arranged with their flat sides facing inward toward one another, and the grooved sides facing outward. Typically, at least one of the rectangular sections is bent into a concave (as viewed from the outside) curve. Typically, the rectangular sections used in illumination system 10 are symmetric sections cut from a central portion of a Fresnel lens. Typically, asymmetric sections cut from near an end of a Fresnel lens may be used in a secondary illumination system, such as in meniscus illumination system 36.

Figure 2:
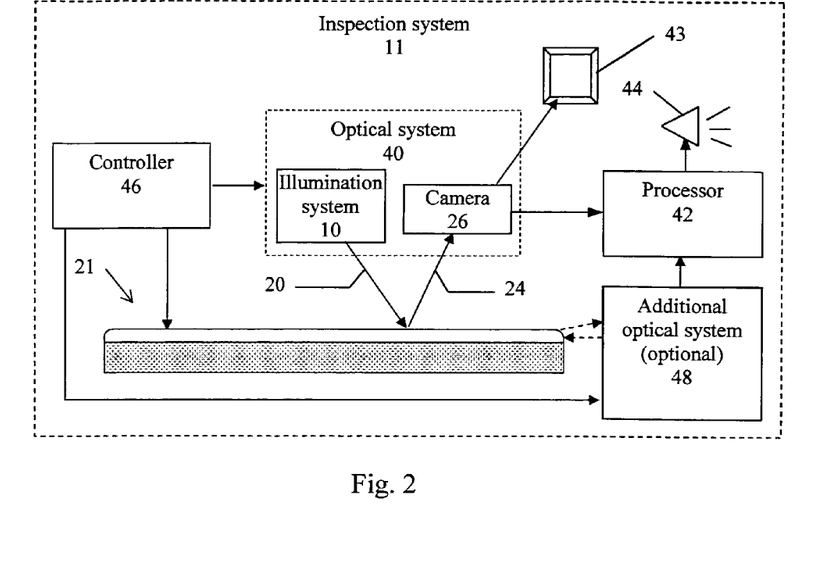
FIG. 2 shows a block diagram of a surface scanning apparatus in accordance with embodiments of the present invention.

FIG. 2 shows a block diagram of a surface scanning apparatus in accordance with embodiments of the present invention. Controller 46 may control electrically controllable components of inspection system 11. Controller 46 may include one or more separate controller subunits, each controlling a subset of the electrically controllable components. The separate controller subunits may communicate or otherwise cooperate with one another so as to coordinate control of the various subunits. For example, controller 46 may control motion of a transport system for transporting or positioning a product to be inspected by inspection system 11, for example, ceramic tile 21.

Controller 46 may control components of optical system 40. For example, controller 46 may control variable components of illumination system 10. For example, controller 46 may control the operation of a light source 12 (FIG. 1) or the size of variable aperture 17 of variable aperture iris 16 (FIG. 1). Controller 46 may control components of illumination system 10 so as to optimize illumination of a particular illuminated surface. For example, optimized illumination may improve the contrast in an image of the surface to as to improve the visibility of a defect against a background of intentional surface features. Controller 46 may also control one or more components of an image acquisition device, such as camera 26. For example, controller 46 may determine when camera 26 is to acquire data, for example, to record a line image. Controller 46 may also control an optional additional scanning system 48. An additional scanning system 48 may be configured to scan an additional surface of ceramic tile 21, for example, meniscus camera 34 and meniscus illumination system 36 configured to scan meniscus 30 of ceramic tile 21 (FIG. 1).

Image data acquired by camera 26 of optical system 40, or by optional additional optical system 48, may be transmitted to a processor 42. Processor 42 may process the acquired data so as to automatically identify a detected defect in a surface of an inspected product such as ceramic tile 21. For example, processor 42 may run a defect or feature detection image processing program, as is known in the art. Processor 42 may include one or more processor subunits. For example, each subunit may be designed to perform a subset of the processing steps performed by processor 42, or to processor a subset of the data processed by processor 42.

In the event that processor 42 detects a defect, processor 42 may activate alarm 44. Alarm 44 may include one or more components designed to alert an operator that a defect has been detected. For example, alarm 44 when activated may generate an audible or a visible signal. A visible signal may include an indication of the location of the defect. For example, an image of the inspected surface may be displayed on a suitable display device or monitor with the defect indicated with a suitable visible graphic indication as is known in the art.

Typically, image data acquired by camera 26 of optical system 40 is displayed on display device 43. When illumination of ceramic tile 21 is optimized, defects in a surface of ceramic tile 21 may be readily visible to an operator who is monitoring display device 43.

Figure 3:
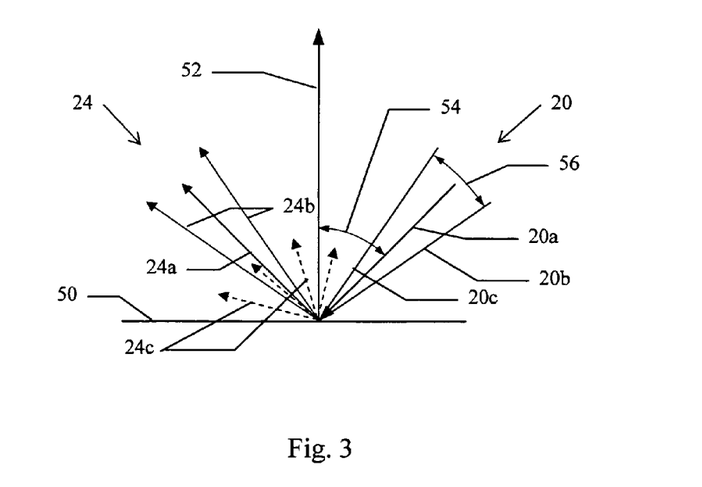
FIG. 3 schematically illustrates concepts related to an illuminating beam.

As stated above, controller 46 may control the configuration of illumination system 10 in order to control the form of illuminating beam 20. FIG. 3 schematically illustrates concepts related to an illuminating beam. Illuminating beam 20 is incident on illuminated surface 50. For example, illuminated surface 50 may be finished surface 22 of ceramic tile 21 (FIG. 1). The orientation of illuminated surface 50 may be defined by the orientation of surface normal 52. Typically, surface normal 52 defines a representative orientation of illuminated surface 50, for example a mean orientation, ignoring local variations in orientation due to intentional surface features. Typically, illuminating beam 20 is in the form of a collimated beam characterized by a divergence angle. For example, the beam may be described by sets of parallel rays, the rays distributed over a region of illuminated surface 50. A representative orientation of the entire illuminating beam 20, for example, a mean orientation of the beam, may be represented by a central ray 20a. The sets of rays differ in orientation from one another. As projected in a plane through a surface normal, the orientations of the various sets of rays differ from one another. The orientations that describe the greatest deviations of the orientations of rays in illuminating beam 20 from the orientation of central ray 20a may be represented by extreme rays 20b and 20c. Thus, a section of illuminated surface 50 is approximately uniformly illuminated with light incident within a range of directions represented by central ray 20a and extreme rays 20b and 20c.

The form of illuminating beam 20 may be defined with reference to a central ray 20a and extreme rays 20b and 20c. Extreme rays 20b may be considered to define the maximum angular deviation of incident light in illuminating beam 20 from the direction of central ray 20a. Angle of incidence 54 may be defined as the angle between surface normal 52 and central ray 20a. Divergence angle 56 may be defined as the angle between extreme ray 20b and extreme ray 20c, representing two extreme directions of illumination in illuminating beam 20.

Illuminating beam 20 may be reflected by illuminated surface 50 to form reflected beam 24. The reflection may be specular, diffuse, or partially specular and partially diffuse. Specular reflection may result in a well-defined reflected beam 24 of reflected radiation that may be represented by a central ray 24a and extreme rays 24b. Diffuse reflection, on the other hand, may result in radiation that is scattered in a wide range of directions represented by diffuse rays 24c.

For example, when an illuminated surface of a product reflects in a diffuse or partially diffuse manner, an edge on the surface due to a variation in surface height may form a shadow. Such a shadow may be detectable by an image acquisition device of a surface scanning system that is pointed at the shadow. The illumination system of the inspection system may be adjusted such that an edge of an intentional feature of the product surface does not form a shadow while an edge of a defect of the surface does form a shadow.

Figure 4A:
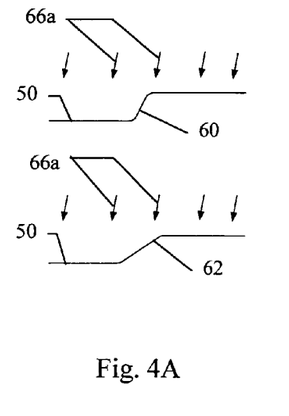
FIG. 4A illustrates illumination of a surface by a parallel beam of illuminating light at a small angle of incidence.

FIG. 4A illustrates illumination of a surface by a parallel beam of illuminating light at a small angle of incidence. Illuminated surface 50 includes defect edge 60 of a surface defect, and feature edge 62 of an intentional feature. Defect edge 60 has a greater slope than, is steeper than, feature edge 62. For the sake of compactness, a section of illuminated surface 50 that includes defect edge 60 and a second section that includes feature edge 62 are shown above one another, rather than as two parts of a single surface. Illuminated surface 50 is shown being illuminated with illuminating radiation 66a with an angle of incidence that is steeper than defect edge 60. For example, an illumination system may be configured to form a small angle of incidence and a small divergence angle. All parts of surface 50 are illuminated and no shadows are formed.

Figure 4B:
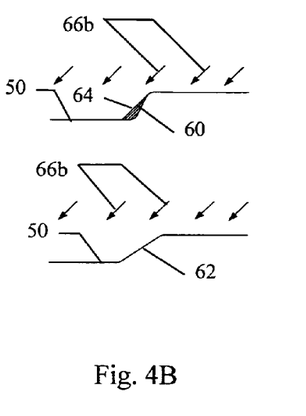
FIG. 4B illustrates illumination of a surface by a parallel beam of illuminating light at an intermediate angle of incidence.

FIG. 4B illustrates illumination of a surface by a parallel beam of illuminating light at an intermediate angle of incidence. Illuminating radiation 66b is incident at an angle of incidence that is shallower than defect edge 60 but steeper than feature edge 60. For example, illuminating radiation 66b may represent a subset of the rays of an illuminating beam with a large divergence angle. Illuminating radiation 66b is blocked by defect edge 60 but not by feature edge 62. Therefore, defect edge 60 is not illuminated, forming shadow 64. Shadow 64 may be detectable by an image acquisition device, resulting in detection of defect edge 60 but not of feature edge 62.

Figure 4C:
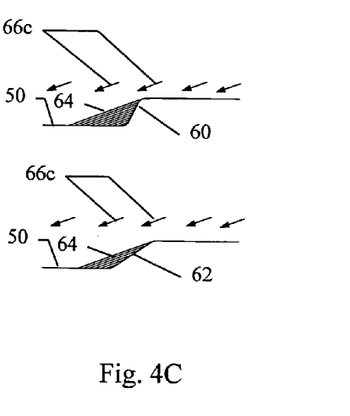
FIG. 4C illustrates illumination of a surface by a parallel beam of illuminating light at a large angle of incidence.

FIG. 4C illustrates illumination of a surface by a parallel beam of illuminating light at a large angle of incidence. Illuminating radiation 66c has an angle of incidence that is shallower than both feature edge 62 and defect edge 60. Therefore, both defect edge 60 and feature edge 62 form shadows 64. Therefore, an image acquired of illuminated surface 50 may not provide sufficient contrast to enable distinguishing between defect edge 60 and feature edge 62. Therefore, the surface scanning system may either not enable identification of defect edge 60 as a defect (false negative result), or may cause erroneous identification of feature edge 62 as a defect (false positive result).

Figure 5A:
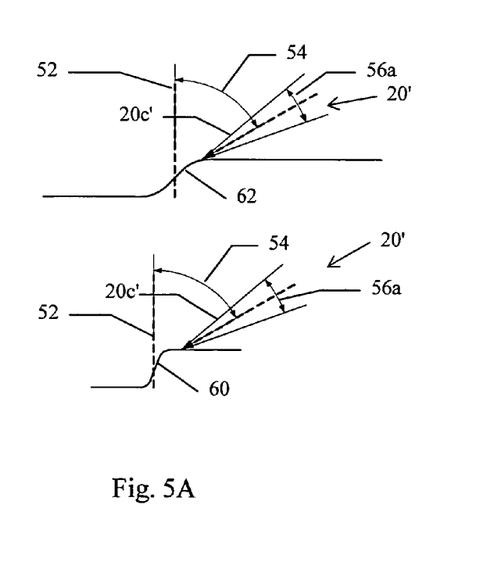
FIG. 5A illustrates an illuminating beam with a narrow divergence angle illuminating a surface.
Figure 5B:
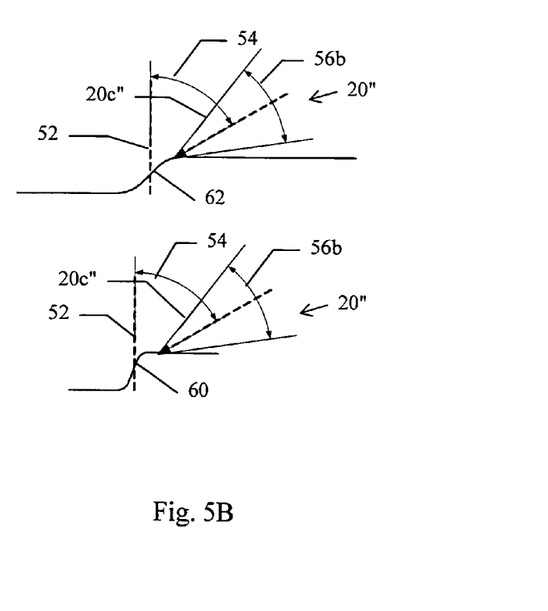
FIG. 5B illustrates an illuminating beam with an intermediate divergence angle illuminating a surface.

An illumination system when optimized, therefore, may generate an illuminating beam that includes illuminating radiation 66b (FIG. 4B), but not illuminating radiation 66c. For example, the divergence angle of the beam may be adjusted such that the beam includes illuminating radiation 66b but not illuminating radiation 66c. FIG. 5A illustrates an illuminating beam with a narrow divergence angle illuminating a surface. Divergence angle 56a is sufficiently small such that the incidence angle of upper extreme ray 20c' of illuminating beam 20' is shallower than feature edge 62. Thus, illuminating beam 20' is entirely blocked by both feature edge 62 and defect edge 60. In this case, both feature edge 62 and defect edge 60 may form shadows. FIG. 5B illustrates an illuminating beam with an intermediate divergence angle illuminating a surface. Divergence angle 56b is sufficiently wide that upper extreme ray 20c" of illuminating beam 20" is steeper than feature edge 62, but shallower than the slope of defect edge 60. Thus, feature edge 62 is at least partially illuminated by illuminating beam 20", while defect edge 60 is not illuminated at all. Thus, defect edge 60 may form a darker shadow that may be visible in an acquired image, while feature edge 62 may form a pale shadow in an acquired image.

The darkness of a shadow in an acquired image may also be affected by illumination in planes other than that shown in FIG. 4B.

A method of optimizing the divergence angle of a beam for a product surface may begin with acquiring an image of a product surface with a beam having a wide divergence angle. For example, a variable aperture may be opened to form a wide opening. With a wide divergence angle, feature edges may not form a shadow. Typically, for the purpose of optimizing the beam, a product surface with no defects (as determined using other means, such as close visual inspection, perhaps under magnification) may be selected. Alternatively, a product surface with known defects may be selected. Successive images are then acquired of the surface while illuminated with beams having successively narrower divergence angles. For example, a variable aperture may be reduced in size. With a sufficiently narrow divergence angle, the feature edges begin to form shadows and to become visible, or prominently visible, in the acquired image. The divergence angle at this point may be set to its value when the image before the last (with visible features) was acquired. The divergence angle (or aperture opening) may remain at this value as other surfaces of products of the same design are scanned. The value of parameters defining this optimum configuration of the illumination system may be recorded. Thus, when a surface of a product of the same product design is scanned in the future, the optimum configuration may be set without performing the optimization procedure.

Figure 6A:
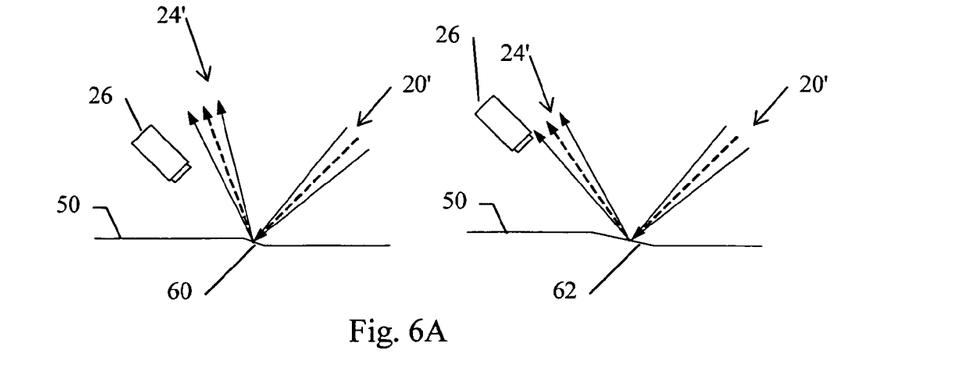
FIG. 6A illustrates illumination of a specular surface by an illuminating beam with narrow divergence angle.

The configuration of an illumination system may also be optimized to produce an illuminating beam that is optimized for illuminating defects on a specularly reflecting surface. Typically in such a case, the axis of an illuminating beam generated by the illumination system and the line of sight of an image acquisition device form approximately equal and opposite angles with a normal to the surface. Thus, in the absence of variations in surface slope, the beam is reflected directly toward the image acquisition device. FIG. 6A illustrates illumination of a specular surface by an illuminating beam with narrow divergence angle. A portion of narrow illuminating beam 20' is reflected by specular illuminated surface 50 to form narrow reflected beam 24'. The orientation of narrow reflected beam 24' depends on the local slope at the point of illuminated surface 50 where narrow illuminating beam 20' is incident. In this case, the entire narrow reflected beam 24' misses camera 26, whether reflected from defect edge 60 or from feature edge 62. In this case, both defect edge 60 and feature edge 62 may appear in an acquired image as unilluminated regions of the surface.

Figure 6B:
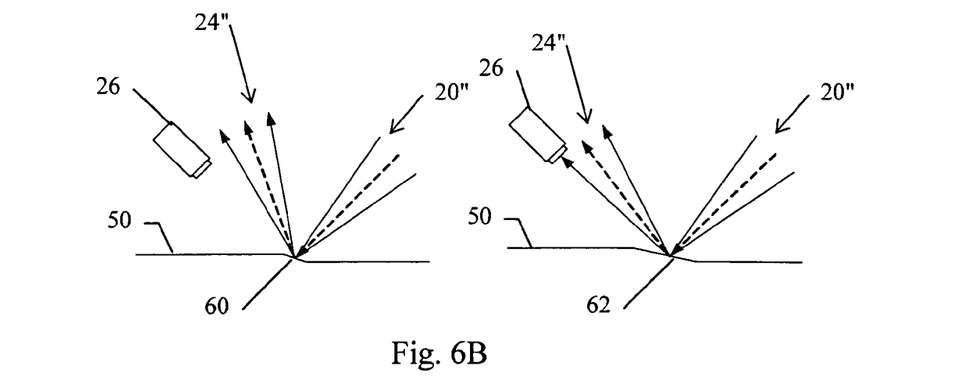
FIG. 6B illustrates illumination of a specular surface by an illuminating beam with intermediate divergence angle.

FIG. 6B illustrates illumination of a specular surface by an optimized illuminating beam. A portion of optimized illuminating beam 20" is reflected by specular illuminated surface 50 to form a reflected beam 24". In this case, part of reflected beam 24" reflected by feature edge 62 may enter camera 26. However, when reflected by defect edge 60, reflected beam 24" misses camera 26. Therefore, in an image acquired by camera 26, defect edge 60 may appear as an unilluminated region of illuminated surface 50. Edge 62, on the other hand, appears illuminated, possibly indistinguishable from the remainder of illuminated surface 50.

Figure 6C:
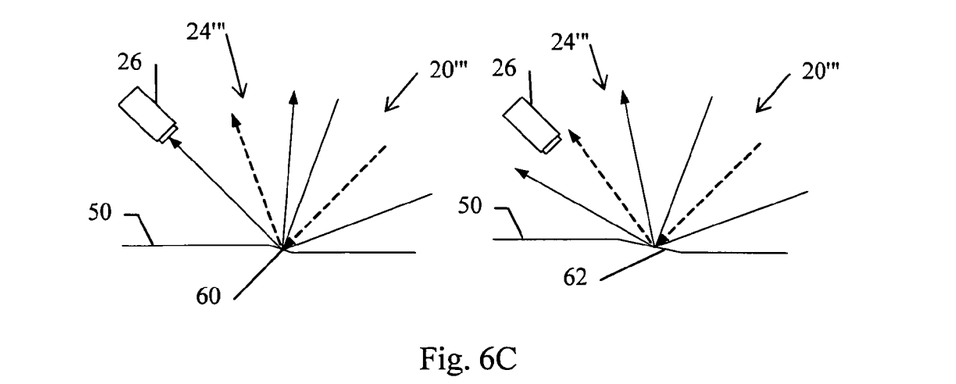
FIG. 6C illustrates illumination of a specular surface by an illuminating beam with wide divergence angle.

FIG. 6C illustrates illumination of a specular surface by an illuminating beam with wide divergence angle. Wide illuminating beam 20' is reflected by specular illuminated surface 50 to form wide reflected beam 24". In this case, a portion of wide reflected beam 24" enters camera 26 whether reflected from defect edge 60 or from feature edge 62. In this case, in an image acquired by camera 26, both defect edge 60 and feature edge 62 appear illuminated, possibly indistinguishable from the remainder of illuminated surface 50. In this case, distinguishing defect edge 60 from feature edge 62 in the acquired image may be difficult or impossible, possibly leading to either a false positive or a false negative result.

A method for optimizing a beam configuration for illuminating a specularly reflecting surface is similar to the method described above for optimizing a beam for illumination of a diffusely reflecting surface. A typical surface is neither completely diffusely reflecting (matte) nor completely specularly reflecting (glossy). In any case, the optimization method is similar.

A surface scanning system in accordance with some embodiments of the present invention may be designed to scan using several beam configurations simultaneously. For example, illuminating beams of various divergence angles may be generated and detected simultaneously for simultaneous inspection for different types of defects or features with different scales. For example, an image acquisition device, such as a camera, may be provided with several types of sensors, each sensitive to a different spectral range. For example, in a typical red-green-blue (RGB) color imaging camera, the sensor surface includes sensors separately sensitive to red, green, and blue light. For example, an illumination system may be configured to simultaneously generate red, green, and blue colored illumination, where each colored illumination has a different divergence angle. Such a configuration may be achieved, for example, with a stack of spectral filters with apertures, or with a light source including a collection of colored light sources.

Figure 7:
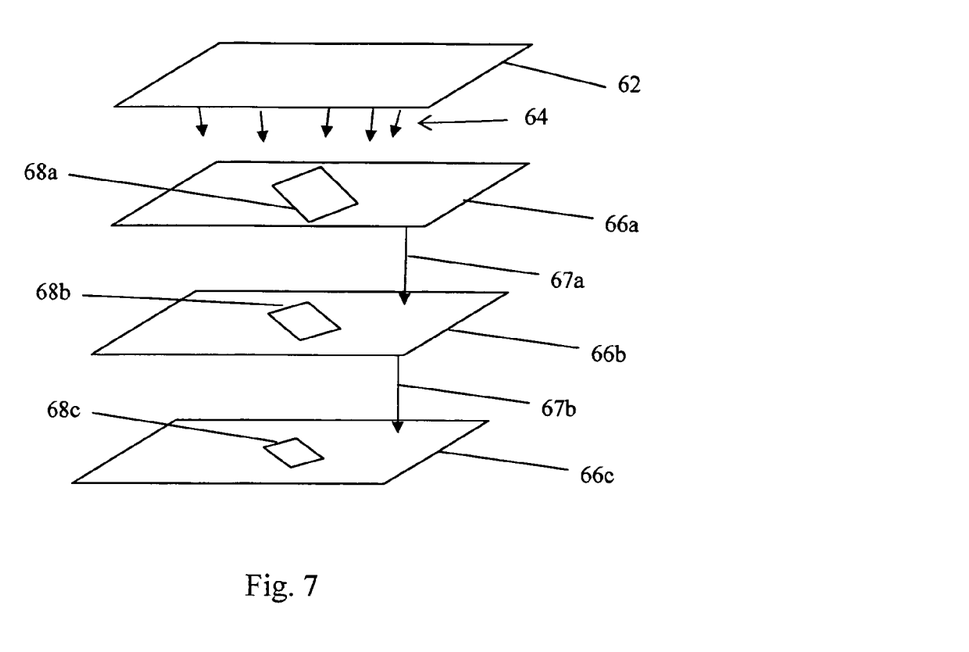
FIG. 7 is a schematic illustration of an illumination system with a stack of spectral filters with apertures, in accordance with some embodiments of the present invention.

FIG. 7 is a schematic illustration of an illumination system with a stack of spectral filters with apertures, in accordance with some embodiments of the present invention. Diffuse illumination source 62, typically including a light source and diffuser, may produce diffuse light that includes components in more than one spectral range. For example, diffuse illumination source 62 may produce diffuse white light 64. Diffuse white light 64 may be considered to include, inter alia, red, green, and blue components. Colored filter 66a blocks a single component of diffuse white light 64. For example, colored iris 66a may be constructed of a transparent yellow material that blocks transmission of blue light. Colored filter 66a transmits red and green light 67a (yellow light), while transmission of blue light is limited by wide aperture 68a. Similarly, colored filter 66b may block another component of red and green light 67a. For example, colored filter 66b may be constructed of a magenta transparent material that blocks transmission of green light. Thus, colored filter 66b transmits red light 67b, as well as any blue light that was transmitted by wide aperture 68a. Transmission of green light is limited by medium aperture 68b. Finally, colored filter 66c may be constructed of a transparent cyan material that blocks red light. Thus, any blue or green light that was transmitted by wide aperture 68a or medium aperture 68b is transmitted by colored filter 66c. However, transmission of red light is limited by small aperture 68c. Thus, a blue beam is produced with a wide divergence angle, a green beam with a medium divergence angle, and red beam with a small divergence angle. It should be understood that the order and individual spectral transmittance ranges of the colored filters, as well as the order of the aperture sizes, is given for illustrative purposes only, and any of these could be rearranged with identical or similar function. Typically, the sizes of one or more of apertures 68a, 68b, and 68c may be individually adjustable. A camera that acquires images of the beams as reflected from an illuminated surface may be provided with sensors sensitive to the various spectral ranges of the beams. Thus, a surface scanning system provided with such an aperture stack and camera may concurrently generate separate acquired images produced with different beam configurations.

Figure 8:
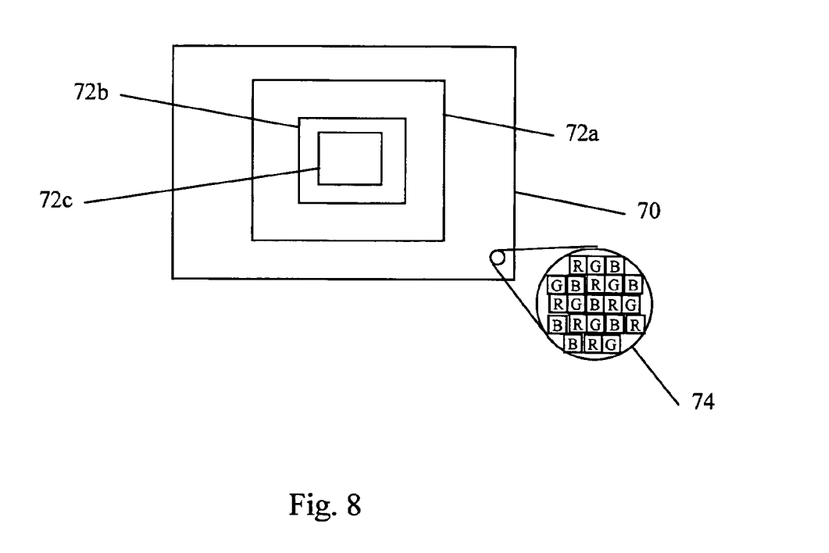
FIG. 8 is a schematic illustration of a light source that includes an array of light sources with different spectral outputs, in accordance with some embodiments of the present invention.

FIG. 8 is a schematic illustration of a light source that includes an array of light sources with different spectral outputs, in accordance with some embodiments of the present invention. For example, multicolored light source 70 may include an array of individual light sources, each individual light source emitting light in a separate spectral range. Each individual light source, or predefined groups of individual light sources, may be turned on or off separately. For example, multicolored light source 70 may include, as shown in magnified region 74, an array of interspersed red (R), green (G), and blue (B) light emitting diodes (LEDs), each individually controllable. For example, one may wish to produce a blue beam with a wide divergence angle, a green beam with a medium divergence angle, and red beam with a small divergence angle. In such a case, blue LEDs may be turned on within rectangle 72a of multicolored light source 70, green LEDs within rectangle 72b, and red LEDs within rectangle 72c. Thus, rectangle 72c may appear white light (red, green and blue together), rectangle 72b outside of rectangle 72b may appear cyan (blue and green), and rectangle 72a outside of rectangle 72b may appear blue. It should be understood that the particular arrangement and the spectra of light emitted by the individual light sources is given for illustrative purposes only, and any other pattern or combination of spectral light sources may be used with identical or similar function. For example, one or more of the individual light source types may emit infrared radiation.

Thus, a surface scanning device is provided for producing a beam that is configurable to optimize the detection of defects in a product surface.

It should be clear that the description of the embodiments and attached Figures set forth in this specification serves only for a better understanding of the invention, without limiting its scope.

It should also be clear that a person skilled in the art, after reading the present specification could make adjustments or amendments to the attached Figures and above described embodiments that would still be covered by the present invention.

The invention claimed is:

1. A surface scanning device for inspecting a product surface comprising:
   an illumination module for illuminating an area of the product surface, the illumination module including a light source, a diffuser, a converging element, and an adjustable aperture iris located between the light diffuser and the converging element, such that the illumination module illuminates the area with illumination of substantially uniform illuminance and with a range of angles of incidence of the illumination on the area that is adjustable by adjustment of the aperture iris; and
   an image acquisition device for imaging the illuminated area.

2. A device as claimed in claim 1, wherein the adjustable range of angles of incidence is selectable from two or more ranges of angles of incidence.

3. A device as claimed in claim 1, wherein the diffusing power of the diffuser is adjustable.

4. A device as claimed in claim 1, wherein the converging element comprises a converging lens.

5. A device as claimed in claim 4, wherein the lens comprises one or more Fresnel lenses.

6. A device as claimed in claim 5, wherein at least one of said one or more Fresnel lenses is curved.

7. A device as claimed in claim 5, wherein said one or more Fresnel lenses comprises two adjacent Fresnel lenses, and wherein flat surfaces of the two Fresnel lenses face each other.

8. A device as claimed in claim 1, wherein the image acquisition device comprises a line camera.

9. A device as claimed in claim 1, wherein the illumination module and the image acquisition device are arranged such that an axis of a beam of illumination produced by the illumination module and a line of sight of the image acquisition device form substantially equal and opposite angles with a normal to the product surface.

10. A device as claimed in claim 1 wherein a location and orientation of the illumination module, the image acquisition device, or both is adjustable.

11. A device as claimed in claim 10, wherein the illumination module comprises a stack of spectral filters, each spectral filter of the stack configured to block transmission of at least one of the different spectral ranges while transmitting at least one of the different spectral ranges, each spectral filter including an aperture for transmitting all of the different spectral ranges.

12. A device as claimed in claim 11, wherein the aperture of a spectral filter of the stack of spectral filters is adjustable.

13. A device as claimed in claim 1, wherein the illumination module produces illumination in at least two different spectral ranges, each spectral range having separately configurable range of angles of incidence, and the image acquisition device includes sensors each responsive to one of the different spectral ranges.

14. A device as claimed in claim 13, wherein the illumination module comprises an array of sources of illumination, each source of illumination configured to produce illumination in one of the different spectral ranges, the sources being controllable such the sources in a region of the array producing illumination in one of the different spectral ranges may be turned on independently of sources in other regions of the array, and independently of sources producing illumination in a different spectral range.

* * * * *